United States Patent [19]

Goffe, deceased et al.

[11] 4,050,898
[45] Sept. 27, 1977

[54] INTEGRAL ANALYTICAL ELEMENT

[75] Inventors: Charles A. Goffe, deceased, late of Brockport, N.Y., by Patricia A. Goffe, executrix; Royden N. Rand; Tai W. Wu, both of Rochester, N.Y.

[73] Assignee: Eastman Kodak Company, Rochester, N.Y.

[21] Appl. No.: 680,619

[22] Filed: Apr. 26, 1976

[51] Int. Cl.$^2$ .............................................. G01N 31/22
[52] U.S. Cl. .............................................. 23/253 TP
[58] Field of Search ................ 23/253 TP; 195/103.5

[56] References Cited

U.S. PATENT DOCUMENTS

| | | | |
|---|---|---|---|
| 3,652,225 | 3/1972 | Coffin, Jr. et al. ................ | 23/230 R |
| 3,875,014 | 4/1975 | Forgione ........................ | 23/253 TP X |
| 3,917,452 | 11/1975 | Rittersdorf et al. ............ | 23/253 TP X |
| 3,929,580 | 12/1975 | Forgione et al. .............. | 23/253 TP X |

OTHER PUBLICATIONS

Research Disclosure, Oct. 1974, pp. 51–56.

*Primary Examiner*—Robert M. Reese
*Attorney, Agent, or Firm*—R. P. Hilst

[57] ABSTRACT

Analytical element for the detection of an agent under analysis, termed analyte, dissolved in an aqueous, proteinaceous liquid. The element has at least two superposed layers, the layers including a spreading layer and a reagent layer. The element can include a support material which is preferably radiation transmissive. To normalize transport of the analyte in and through the spreading layer, the spreading layer contains an effective amount of a surfactant, such as a non-ionic surfactant. Preferably, the amount of surfactant is between about 1% and about 15% by weight of solid contents in the spreading layer.

23 Claims, 7 Drawing Figures

18 SPREADING LAYER
16 FILTERING LAYER
14 REFLECTING LAYER
12 REAGENT LAYER
10 SUPPORT

- 18 SPREADING LAYER
- 16 FILTERING LAYER
- 14 REFLECTING LAYER
- 12 REAGENT LAYER
- 10 SUPPORT

- 24 SPREADING LAYER
- 22 REAGENT LAYER
- 20 SUPPORT

- 36 SPREADING LAYER
- 34 DIALYSIS LAYER
- 32 REAGENT LAYER
- 30 SUPPORT

INTEGRAL ANALYTICAL ELEMENT

BACKGROUND OF THE INVENTION

1. Field of the Invention

Chemical analysis of liquids such as water, foodstuffs like milk, and biological liquids is often desirable or necessary. Various elements to facilitate liquid analyses are known. Such elements have often included a reagent for a substance under analysis, termed analyte herein, which reagent, upon contacting a liquid sample containing the analyte, effects formation of a colored material or another detectable change in response to the presence of the analyte. Such elements include, for example, pH test strips and similar indicators wherein a paper or other highly absorbent carrier is impregnated with a material, chemically reactive or otherwise, that responds to contact with liquid containing hydrogen ion or other analyte and either generates color or changes color. Depending on the selection of responsive material, the change is usually qualitative or, at best, semiquantitative. In certain fields, it is often required that analytical techniques yield rapid, quantitative results. Much recent development work has attempted to provide elements useful in diagnostic chemical analysis, where testing of biological liquids including body fluids such as blood, blood serum, urine and the like, must produce highly quantitative results, rapidly and conveniently.

Solution chemical techniques have enjoyed broad acceptance in the clinical laboratory environment, particularly in automated analysis. Such techniques, however, require analyzer equipment often having intricate solution handling and transport capabilities. Analytical equipment of the "wet chemistry" variety, illustrated, for example, in U.S. Pat. No. 2,797,149 can involve complex liquid handling, and may require skilled personnel, both for operation and the precise cleaning that may be needed to avoid sample to sample contamination.

As an alternative to solution chemistry, various multilayer integral elements for non-solution chemical analysis have been proposed. Although essentially dry analysis can offer substantial storage, handling and other conveniences as compared to wet chemistry, variations of the "dry" approach have enjoyed only limited success and have been used primarily for qualitative and semiquantitative test purposes.

2. Description of Related Art

A basic variety of integral elements is described in U.S. Pat. No. 3,092,465. Such multilayer elements use an absorbent fibrous carrier, such as filter paper, impregnated with one or more reagents, typically including a color former, over which is coated a semipermeable membrane. Upon contact with a test liquid, analyte passes through the membrane which prevents passage and absorption into the fibrous carrier of certain interfering components, such as blood cells, that could impair the test result.

Analytical elements that rely on absorbent filter papers or other fibrous media to receive and distribute a liquid sample have not been popular, compared to wet chemical procedures, in applications such as clinical laboratory testing, presumably due to their inability to produce highly accurate, quantitative results. As used herein, the term "fibrous" as applied to materials such as papers and the like refers to materials having discrete fibers, filaments or strands. Exemplary fibers and fiber forms used in preparing analytical elements using various fibrous materials are described, for example, in U.S. Pat. Nos. 3,802,842 and 3,867,258.

It is described in the literature that diagnostic elements using impregnated bibulous materials, such as filter papers, can produce non-uniform test results. In U.S. Pat. No. 3,050,373, it is mentioned that precipitation can occur in the impregnating solutions thereby impairing uniform distribution of reagent within the bibulous matrix. Also, elements using such fibrous, bibulous materials are susceptible to the occurrence of a non-uniform test result phenomenon termed "banding", apparently a deleterious diffusion and chromatographing of reagent chemicals or analyte within the bibulous material.

Integral analytical elements useful in automated test procedures are described in U.S. Pat. Nos. 3,368,872 and 3,526,480. Although, in the 3,526,480 patent, gel matrix materials are discussed as useful for reagent-containing layers, fibrous materials are also described and illustrated. Fibrous materials are also used in reagent layers mentioned in the 3,368,872 patent.

A more recent discussion of an analytical test device using fibrous materials appears in U.S. Pat. No. 3,791,933, which describes a multi-component device for the assay of enzyme substrates and metabolites, such as in body fluids. The device is a clamped array adapted to receive a test sample, filter out or otherwise remove large sample constituents (such as proteins) and effect a test reaction to produce a detectable result, such as the generation of a color. Glass fiber paper is disclosed as assisting in distributing a reaction mixture across a plastic viewing window, preferably porous to minimize lamination problems caused by air entrapment. The glass fiber material apparently merely assists the outward diffusion of liquid sample within that layer, to enlarge the region of the element exhibiting a test result and thereby render the result more easily discernible.

Test devices relying on fibrous matrix materials have exhibited various problems, such as the banding phenomenon referred to previously. As is apparently recognized, the chemical characteristics of the fibrous, bibulous materials (such as absorbent cellulosic filter papers, glass fiber papers, wood, etc) usually proposed as a preferred matrix material for integral analytical elements might impair the accuracy of an analytical result for reasons of chromatographic effects, physical restraint, non-uniform capillary migration or other non-uniform permeation of sample constituents, or for reasons of undesirable chemical binding. Additionally, fibrous materials can generate bias and frustrate highly accurate measurement of an analytical result when the fibrous material is observed by a detection means, due to variations in its properties such as structure, texture and apparent reflectance as seen by a detector for electromagnetic radiation. In the preparation of papers, which appear to be the most popular fibrous matrix material for analytical elements, larger starting fibers are often processed to form smaller tendrils that strengthen the resultant paper.

Various means have been suggested to overcome the banding and other undesirable effects associated with the presence of fibrous matrices in analytical elements. Gelatin and other such materials are described in U.S. Pat. Nos. 3,061,523 and 3,104,209 as useful constituents of impregnating solution for fibrous, bibulous materials, due to the inhibitory effect on banding. However, gelatin and gelatin-like materials in the fibrous, reagent-containing bibulous matrix decrease the rate of sample uptake as compared to a more highly absorbent gelatin-free matrix. Such decreased absorption can leave surface liquid on such test elements and can necessitate washing the element to remove excess sample prior to making a test determination. As a result, upper limits on gelatin concentration have been specified. Such absorption is considered characteristic also of analytical elements using layers solely of gelatin or similar materials, as discussed in U.S. Pat. No. 3,526,480.

In another aspect, it has been suggested, as in U.S. Pat. Nos. 3,368,872 and 3,526,480, that undesirable chromatographic effects can be decreased by immobilization of reagents in an element or by including therein a means to decrease the tendency of spotted or otherwise applied sample to exert a washing effect on incorporated reagent, as by use of certain porous members over an absorbent, reagent-containing material such as fibrous filter paper.

The disturbing effects of banding and the like are referred to also in U.S. Pat. Nos. 3,552,929 and 3,802,842 which propose, respectively, a polymeric coating and meshwork overlayer to be used in connection with fibrous reagent-containing layers in order to minimize such effects.

In pseudo-immersion technique, which can be termed spot confinement, has also been suggested as a means of providing sample-to-sample test result precision, such as between a proteinaceous test liquid and a protein-free calibrator. In accordance with this technique, as is described, for example, in U.S. Pat. Nos. 3,216,804, 3,368,872 and 3,526,480, a barrier is usually included on the element to confine the applied sample, such as a small drop, in a predetermined region of the element's surface. Excess liquid is usually present on the element after sample application. This can create inconvenience in handling if the element is integral and, more seriously, can require precise sample volume delivery when applying sample to the element if test accuracy and precision are to be maintained.

There has been some recognition of the need to promote or avoid, as desired, the migration of reagents and sample constituents, such as between layers of integral analytical elements, for example, as is discussed in U.S. Pat. Nos. 2,761,813; 2,672,431; 2,672,432; 2,677,647; 2,923,669; 3,814,670 and 3,843,452. However, this has generally been in the context of elements for determining the presence of micro-organisms. Such elements generally do not indicate any means to effect or preserve concentrational uniformity, for example, laterally within a layer, and they can require blended layers, the interface of which is characterized by mutual penetration of the adjacent layers.

Until very recently, there has been no effective suggestion in art relating to analytical elements of a layer or other means to receive sample constituents and encourage them to distribute within that means to achieve an apparent concentrational uniformity of analyte, analyte product or other substances that can be metered, in such uniform apparent concentration, to an associated layer for analytical reactions or similar activity. Devices using fibrous materials to provide absorbent layers have sought to overcome the gross effect of such non-uniformity, but they have not succeeded in avoiding the problem. As an example, U.S. Pat. No. 3,715,192 describes an analytical element that provides a hollow space in communication with the surface of a reagent impregnated, preferably fibrous, absorbent capillary material. The hollow space apparently effects more rapid absorption of liquid into the capillary material and minimizes the washing out and chromatographing of reagents, thereby enabling an increased use of reagents that are soluble in liquid under analysis. Also, U.S. Pat. No. 3,723,064 describes an analytical element that includes regions of different effective permeability to an analyte or reaction product of an analyte and produces a plurality of differential, threshold color indications as an analytical result. Although the desirability of a smoothly continuous response is manifest, an element made in accordance with the 3,723,064 patent can only yield an approximate analytical result, the accuracy of which varies inversely with the spacing between thresholds. As the difference in permeability between regions is decreased, in the interest of increased response precision over the intended dynamic range, the complexity of elements made in accordance with the 3,723,064 patent would increase dramatically. Moreover, no suggestion is made as to how one might improve the uniformity and precision of a continuously varying test result and, however, optimized, elements of the 3,723,064 patent would produce a discontinuous response that would apparently be non-uniform within each region of permeability due to non-uniformities associated with the use of filter papers and other fibrous materials.

Improved multilayer integral analytical elements are described in Belgian Pat. No. 801,742. Such elements, preferably formed predominantly from non-fibrous components, can receive a liquid sample and effect distribution of the sample within a spreading layer of the element to obtain a uniform apparent concentration of analyte, other appropriate sample constituent or analyte product and produce uniform, typically quanititative analytical results that, by virtue of their accuracy and precision, can be measured reliably by automated devices, using techniques such as spectrophotometry, fluorometry, etc. Elements disclosed in Belgian Pat. No. 801,742 include spreading layers and reagent layers that contain a reactive or otherwise interactive material that, by virtue of its activity, promotes in the element a radiometrically detectable change, such as a color change.

It has been found that the analytical result obtained using elements of the general type described in Belgian Pat. No. 801,742, adapted to test proteinaceous, aqueous liquids for water-soluble analytes dissolved therein, can be affected by the protein concentration of such liquids. More particularly, it is believed that increased protein concentration can restrain the rate and extent of liquid and analyte transport within the spreading layer and the rate of such transport through the spreading layer. For a given sample volume, more highly proteinaceous analyte-positive liquids produce initially a test result indicating a lower analyte concentration in the sample than would occur at lower protein concentrations and, thereafter, usually produce a test result indicating a higher analyte concentration than would occur at lower protein concentrations. These results are believed to occur due to a restraint in the transport of a sample's solvent and dissolved components within the spreading layer, producing initially in an analyte-positive sample a slower contact of analyte to the indicator composition or other reagent chemistry and producing thereafter a somewhat smaller wetted region for any given sample size. When the indicating reaction is allowed to proceed substantially to completion, a greater amount of analyte is provided to each incremental unit of the sample affected portion of a reagent layer and produces a higher indicated analyte. For accurate determinations, variability in result introduced by protein differences could require that in each instance a protein assay be made to calibrate the analyte assay. Such procedures would be time consuming and add a potential source of error to the analyte determination.

It has been discovered that various surfactant materials can, when included in an effective amount within particularly the spreading layer of elements as described in Belgian Pat. No. 801,742 and in other patents and applications based on the same invention such as U.S. Patent Application Ser. No. 538,072, filed Jan. 2, 1975, inhibit the protein effect discussed above and elsewhere herein.

Surfactants have been described previously in relation to analytical elements. Research Disclosure Publication Volume 126, Item 12626 (October, 1974) refers to analytical elements of the type described in Belgian Pat. No. 801,742 that are intended to analyze liquids for their cholesterol content, using the enzyme cholesterol oxidase. It is described that, in such elements, nonionic surfactants can be used as a coating aid. No concentrations are specified, but about 0.1% is referred to in the 801,742 Belgian patent as useful for such purposes. Also, the publication mentions that it is important that such a surfactant be in the presence of the cholesterol oxidase to assure the complete oxidation of cholesterol. No suggestion is made that the surfactant would be useful in analytical elements for any other purpose or in an analytical element intended for the determination of dissolved analytes. Cholesterol is not dissolved in serum but is transported via associations with lipoproteins. The use of surfactants to disassociate cholesterol esters/protein complexes is also discussed in U.S. Pat. No. 3,907,645.

Surface-active agents are also described in U.S. Pat. No. 3,050,373 as useful for enhancing the density of color produced in a bibulous matrix by glucose detection chemistry using a glucose oxidase, peroxidase and a chromogen. The surfactant is also described as an agent that minimizes the previously discussed banding phenomenon. There is no suggestion in the 3,050,373 patent of having a surfactant in other than the layer of an element containing reagent chemicals and both nonionic and anionic surfactants are discussed as being useful. Also apparently useful for color enhancement purposes are hydrophilic colloids containing a polyvinyl chain, such as polyvinylpyrrolidone and polyvinyl alcohol. Wetting agents are also referred to as being useful constituents of reagent layers in U.S. Pat. No. 3,802,842.

The ability to provide improved analytical elements of the type described in Belgian Pat. No. 801,742 to test for analyte dissolved in proteinaceous, aqueous liquids and with minimal differences in test results due to sample-to-sample variations in protein concentration, represents a substantial improvement in the dry chemical analysis of biological liquids.

SUMMARY OF THE INVENTION

The present invention provides novel integral elements for analysis of proteinaceous, aqueous liquids, such as protein-containing biological liquids like blood, blood serum, urine, etc. The present elements are useful in the analysis of analyte dissolved in proteinaceous, aqueous liquids. As used herein, the term integral element refers to elements having at least two superposed layers, desirably discrete, in intimate contact under conditions of use. In one aspect, the layers are essentially inseparable without damage to the element. Elements of this invention are capable of performing internally a variety of sample handling functions. They do not require expertise in their use and they can produce quantitative analytical results without the specialized spotting or other procedures such as sample confinement, washing or removal of excess sample, typically needed for analyses made using known elements. Further, the results produced by elements of this invention are substantially consistent and free from major internal variations so that automated means of measuring electromagnetic radiation (radiometric techniques) can be used to detect such results, if necessary or desirable, with minimal risk of error.

Stated more particularly, the present invention provides analytical elements composed of multiple, superposed layers, which can provide a quantitative, detectable change in response to the presence of an analyte dissolved in proteinaceous liquid applied to the element. The liquid can be applied overall or it can be applied locally as a contact spot or free drop. Localized application is often preferable as less sample is required. Elements of this invention can be used for diagnostic purposes and include a spreading layer and a reagent layer that are in fluid contact under conditions of use.

The spreading layer, synonymously referred to herein as a sample spreading layer or a metering layer, includes a surfactant capable of normalizing transport within the spreading layer of the applied proteinaceous liquid and its dissolved components. Normalization of liquid transport refers to obtaining within the spreading layer an equivalent penetration of the solvent medium and dissolved components of various applied samples of aqueous proteinaceous liquids, notwithstanding variations in protein concentration between such samples. Conveniently determined indices of such equivalence are the rate at which an analytical result is produced and the maximum diameter of the colored spot or other analytical result that is produced in each element. The spot diameter readings are adjusted for differences in volume between applied samples. Desirably, normalization of spreading will produce substantially equivalent rates of result production and spot diameters that vary by not more than about 10% over the anticipated range of sample protein concentration. Spot size variation of less than about ±5% is most preferred. In human serum, for example, proteins are usually present in an amount of from about 6 gram percent to about 8 gram percent, and the concentration may range as high as 12 gram percent in serum taken from a severly dehydrated subject. In the spreading layer, the surfactant is preferably in a concentration effective to obtain normalized spreading over the range of protein concentrations anticipated in samples to be applied to the element.

The various layers of the present elements can be carried on a support that in various preferred embodiments is radiation-transmissive. As used herein, the term "radiation-transmissive" describes supports and other layers of an analytical element that permit effective passage of electromagnetic radiation used to detect an analytical result produced in the element. Such transmissiveness includes transmission of electromagnetic radiation of a wavelength or wavelengths within the region between about 200 nm and 900 nm, and also of detectable radiation as is produced by radioactivity.

Radiation-transmissive layers and supports can be transparent at one or more wavelengths, if desired, and this may be beneficial for measurements to be made at low levels of radiation. When the element includes a support, the reagent layer is interposed between the support and the sample spreading layer.

Spreading layers of the present elements are capable of distributing or metering internally the solvent or dispersion medium of an applied aqueous liquid sample and components carried within the sample including at least a dissolved component to provide, at any given time, a uniform apparent concentration (i.e., a concentration that is apparently uniform as measured by appropriate detection procedures and chemistry such as is discussed below) of one or more spread components at the surface of the spreading layer facing, i.e., closer to, the reagent layer. The applied sample need not be confined, and such apparent concentration, although instantaneously uniform, can change over a period of time without deleterious effects. The term "component" as used herein with reference to a liquid sample refers broadly to an ingredient of the liquid, whether in its free state or as a chemical moiety that is a part of a more complex component. It will be appreciated that such ingredients can be provided in the liquid after its application to the element, such as through appropriate chemical reactions. In various cases, the component may be an analyte or a precursor of an analyte or a reaction product of an analyte. Reaction products of components such as analytes include chemical species that are decomposition or other reaction products of a component, as well as other products derived from a component, such as reaction products formed as the result of the enzymatic activity of an analyte or other component.

The spreading layer is preferably isotropically porous and non-fibrous. Reference herein to isotropic porosity identifies the fact of substantial porosity in all directions with the spreading layer. It will be understood that the degree of such porosity may be variable, if necessary or desirable, for example regarding pore size, percentage of void volume or otherwise. It shall be understood that the term "isotropic porosity" (or "isotropically porous") as used herein should not be confused with the terms "isoporous" or "ionotropic", often used with reference to filter membranes to signify those membranes having pores that are continuous between membrane surfaces. Likewise, isotropic porosity should not be confused with the term "isotropic", used in contradistinction to the term "anisotropic", which signifies filter membranes having a thin "skin" along at least one surface of the membrane. See, for example, *Membrane Science and Technology*, James Flinn ed, Plenum Press, New York (1970).

The reagent layer is a layer containing at least one material that is interactive in the presence of analyte-positive liquid applied to the element. In various instances, the interactive material may be interactive with an analyte or a precursor or a reaction product of an analyte to effect production of a change within the element by virtue of such interactive material. The reagent layer is permeable to at least one sample component spreadable within the spreading layer or to a reaction product of such a component and is preferably of substantially uniform permeability to substances spreadable within the spreading layer. As used in the specification and claims herein, the term "permeable" denotes the ability of a substance or layer to be penetrated effectively by a material carried, i.e., distributed as by being dissolved or dispersed, in a liquid.

Uniform permeability of a layer refers to permeability such that, when a homogeneous liquid is provided uniformly to a surface of the layer, identical measurements of the concentration of such fluid within the layer, but made through different regions of a surface of the layer, will usually yield substantially equal results, e.g., less than about ±10% and preferably less than about ±3-5% when measured radiometrically through a small aperture such as one of about 3-10 microns wide and 50-100 microns long. If a continuous scan is used to make the measurements, a trace magnification of about 16 can be used advantageously to expand the scale.

By virtue of uniform permeability, undesirable concentration gradients can be avoided within, for example, a reagent layer. Uniform permeability of reagent or other appropriate layers within an analytical element is desirable as a means of facilitating the convenient detection of analytical results. It is not necessary that all possible measurement techniques produce such results. The desirability of a particular technique and of specific measurement parameters will depend on the physical characteristics of the layer, such as its tendency to transmit, absorb or scatter radiation. The selection in any instance of an appropriate measurement technique (e.g., colorimetric, densitometric, fluorimetric) and of appropriate measurement parameters (e.g., aperture size and configuration) will be apparent to those familiar with analytical procedures.

As discussed elsewhere herein, uniform permeability is not considered characteristic of fibrous materials such as filter papers, fibrous mats, woven fabrics, etc. It is believed that factors such as variable wicking action within a fibrous material, differences in fiber size, spacing, optical properties, and the like, can effect the formation within such fibrous materials, and also in associated materials in fluid contact therewith, of varying apparent concentrations of components of permeant liquid. This, of course, can introduce undesirable bias between test measurements made within regions having different apparent concentrations of the analyte, dye, fluorescent species or other agent being measured. Analytically significant results may be obtainable in elements not having uniformly permeable layers, but the efficiency of result detection may be impaired, for example, if irregularly occurring concentrational or other discontinuities, seen by a means of detection, are present within an element.

Reference herein to fluid contact between a spreading layer and a reagent layer and/or other layers in an integral analytical element identifies the ability of a fluid, whether liquid or gaseous, to pass in such element between superposed regions of the spreading layer and the reagent layer. Stated in another manner, fluid contact refers to the ability to pass components of a fluid between the layers in fluid contact, and such capability is preferably uniform along an interface between fluid contacting layers. In the case of analysis for nitrogen containing compounds, ammonia or other nitrogen containing gaseous materials may comprise fluid passing between spreading layer and reagent layer. Although layers in fluid contact can be contiguous, they may also be separated by intervening layers. However, layers in the element that physically intervene a spreading layer and reagent layer in mutual fluid contact will also be in fluid contact and will not prevent the passage of fluid between the fluid contacting spreading and reagent layers.

Fluid contact between layers can be achieved by preparing elements having layers that are initially contiguous or effectively so for purposes of fluid passage. Alternatively, it may be appropriate to prepare elements that have layers initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has initially non-contiguous layers, it may be necessary to apply compressive force or otherwise provide means to bring layers of the element into fluid contact at the time of its use to provide an analytical result.

An exemplary analytical element of this invention can receive an analyte-positive liquid sample which is distributed, as discussed elsewhere herein, within the metering layer containing a surfactant of choice in an amount sufficient to normalize liquid transport in that layer. As a result of such distribution, at any given time a uniform apparent concentration of spread sample components is preferably provided at the surface of the metering layer facing a reagent layer. It is possible to obtain such uniform apparent concentration over a wide range of sample volumes applied to the element and, due to the presence of a surfactant of choice in the spreading layer, over an appropriate range of protein concentrations present in liquid under analysis. Components of the sample are provided from the spreading layer to the reagent layer to penetrate the reagent layer essentially without the occurrence therein, at any instant in time, of significant variations in the apparent concentration of such sample components. Having an interactive (e.g., chemically reactive) material within a reagent layer, and a uniform apparent concentration of appropriate sample components provided in the reagent layer, a uniform, quantitative detectable change can be produced in the element. Such a change, which can be the generation or destruction of coloration or fluorescence, can be detected quantitatively by radiometric techniques and, if desired, by automatic radiometric sensing devices such as photometric or fluorometric devices. As is explained elsewhere herein, other layers, such as filter layers, registration layers, and/or reflective layers can be used in association with the spreading and reagent layers.

BRIEF DESCRIPTION OF THE DRAWINGS

In the accompanying drawings, each of FIG. 1, FIG. 2 FIG. 7 is an analytical result produced using an element of the invention.

DESCRIPTION OF PREFERRED EMBODIMENTS

Figure 1:
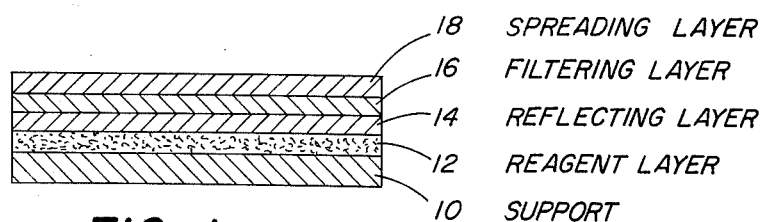

The integral elements of this invention include a spreading layer and a reagent layer. The spreading layer is an isotropically porous, preferably non-fibrous layer, functioning to spread within itself substance including the solvent medium and at least a dissolved component of a liquid sample or a reaction product thereof to provide a uniform apparent concentration of spread component or components at the surface of the spreading layer facing the reagent layer. It will be appreciated that such a concentration can be achieved with concentration gradients present through the thickness of or otherwise in the spreading layer. Such gradients do not present any difficulty to obtaining quantative test results and can be accommodated using known calibration techniques.

The mechanism of spreading is not fully understood, but it is theorized that spreading results from and is limited by a combination of forces such as hydrostatic pressure of a liquid sample, capillary action within the spreading layer, surface tension of the sample, wicking action of layers in fluid contact with the spreading layer, and the like. As will be appreciated, the extent of spreading is dependent, in part, on the volume of liquid to be spread. However, it should be emphasized that the uniform apparent concentration obtained with spreading in layers as described herein is substantially independent of liquid sample volume. As a result, elements of this invention do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., an area of about one centimeter in diameter), there is no need to remove excess moisture from the element after application of a liquid sample. Further, because spreading occurs in the spreading layer and the spread substance is provided to the fluid contacting reagent layer without apparent substantial lateral hydrostatic pressure, there is not the "ringing" problem often seen with prior analytical elements.

The spreading layer need only produce a uniform apparent concentration of spread components per unit area at its surface facing a reagent layer with which the spreading layer is in fluid contact in use, and it is very convenient to determine whether a particular layer can be suitable for spreading purposes. Such uniformity of apparent concentration can be determined by densitometric or other analytical techniques, as by scanning the appropriate surface or reagent layer or other associated layer to determine the apparent concentration of spread components or of any detectable product based on the concentration of spread components. The following test is intended only as an example and the selection of materials or test parameters does not indicate, expressly or by implication, that other materials or parameters would not be suitable for similar purposes.

In conducting such a test, one can apply to a transparent photographic film support material, such as subbed poly(ethylene terephthlate), a transparent gelatin layer at a gelatin coverage of about 200 mg/dm$^2$. The gelatin may vary in hardness, but for testing purposes a layer of gelatin hardened such that the layer thickness swells by about 300% when immersed for 5 minutes in 22° C water is suitable. When dry, the gelatin layer will have a thickness of about 30 microns. Over the gelatin layer can be applied, such as by coating from solution or dispersion, the layer to be evaluated for spreading purposes. Spreading layers can be designed to have widely varying dry thicknesses, and a thickness of about 100 to about 200 microns is convenient for test purposes. After drying the layers, a sample of test solution or dispersion can be applied to the surface of the spreading layer under evaluation, preferably in a small quantity so that not all portions of the layer are wetted by the applied sample, but desirably sufficient to create a wetted region such as one having a circular area of about 8-10 millimeters in diameter. The selection of a test solution or dispersion is a matter of choice and will depend in part on the type of sample or analyte to which the layer will be exposed under conditions of actual usage. For low molecular weight materials, aqueous dye solutions can be used and a .0005 weight percent solution of Solatine Pink$^R$ is acceptable. For higher molecular weight materials such as proteins, an aqueous dispersion of bovine albumin dyed with Solatine Pink$^R$ can be used. After applying the liquid sample to the layer under evaluation and allowing the liquid sample to disappear from the surface of and be taken up into the layer, the test element can be turned over and the bottom surface of the proposed spreading layer can be viewed through the transparent support material and gelatin layer. If, prior to substantial evaporation of solvent or dispersion medium, the test element exhibits a colored, preferably well-defined spot of a substantially uniform color density when scanned by a densitometer having an aperture of about 5 microns by 100 microns, then spreading and the achievement of a uniform apparent concentration at the bottom surface of the test layer and/or in the gelatin layer has taken place. By substantially uniform density is meant a density across the spot, with the exception of its periphery, having maximum and minimum values not more than about ±10% from the mean density. In various preferred embodiments of the invention, the variation in density or other detectable result should not be more than about ±5%. Due to edge effects, non-characteristic density gradients may arise at the spot periphery but need have no effect on the significance of an analytical result. Peripheral area can vary between spots, but it will usually not be more than 20% of the entire spot and may be less.

As mentioned herein, spreading or metering layers can be isotropically porous layers. Such layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such microcrystalline materials are described in an article entitled, "Colloidal Macromolecular Phenomena, Part II, Novel Microcrystals of Polymers" by O. A. Battista et al published in the Journal of Applied Polymer Science, Vol. II, pages 481–498 (1967). Microcrystalline cellulose, which is commercially available from FMC Corporation under the name Avicel$^R$, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non-adherent particles can be coated with a thin adherent layer, such as a solution of hydrophilic colloid like gelatin or polyvinyl alcohol, and brought into mutual contact in a layer. When the colloid coating dries, the layer integrity is maintained and open spaces remain between its component particles.

As an alternative or in addition to using particulate matter, which itself need not be isotropically porous, the spreading layer can be prepared using isotropically porous materials, in the form of particles or otherwise. The isotropically porous materials can be polymeric in composition, such as compositions formed from blush polymers. Techniques for providing blush polymers, also referred to as precipitated or coagulated polymers, are discussed in publications such as U.S. Pat. No. 2,783,894 and 3,555,129.

Other techniques useful in preparing isotropically porous polymer compositions include those relating to the use of gas or other swellable constituents to create porous foams, as described in U.S. Pat. Nos. 2,960,728 and 2,946,095; or to the use within a polymer phase of a dissolvable solid that is dissolved to provide pores, for example, as discussed in U.S. Pat. No. 3,816,575.

Layers comprising blush (or precipitated) polymers are particularly desirable and can be formed on a substrate by dissolving a polymer in a mixture of two liquids, one of which is a lower boiling, good solvent for the polymer and the other of which is of a higher boiling point and is a non-solvent or at least a poor solvent for the polymer. Such a polymer solution is then coated on the substrate, and dried under controlled condition. The lower boiling solvent evaporates more readily and the coating can become enriched in the liquid which is a poor solvent or non-solvent. As evaporation proceeds, under proper conditions, the polymer forms as an isotropically porous layer. Many different polymers can be used, singly or in combination, for preparing isotropically porous, blushed polymer spreading layers for use in this invention, typical examples being polycarbonates, polyamides including nylons, polyurethanes, and cellulose esters like cellulose acetate.

In accordance with the present invention, the spreading layer contains one or more surfactant materials effective in normalizing liquid transport in the spreading layer. A broad variety of ionic and nonionic surfactants can be useful. Of the ionic surfactants, preferred are anionic surfactants like alkali metal alkyl sulfates, where the alkyl moiety has more than 8 and usually between 10 and 20 carbon atoms, such as sodium dodecyl sulfate. Especially desirable are nonionic surfactants, many examples of which are set out in McCutcheon's *Detergents and Emulsifiers*, 1974 North American Edition by the Allured Publishing Corporation.

Preferred nonionic surfactants include alkarylpolyethers, such as alkylphenoxypolyethoxyethanols like those having the following formula I:

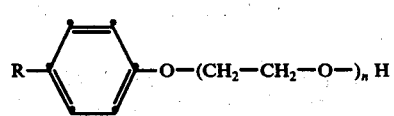
(I)

where R represents an alkyl group, such as one having from 1 to about 9 carbon atoms and $n$ represents an integer having a value of from 5 to about 40. A wide variety of such surfactants are useful, such as the octyl- and nonyl-phenoxy polyethoxy ethanols of formula I wherein R represents an octyl group or a nonyl group. In one preferred embodiment, R represents an octyl group and n represents an integer df from about 9 to about 40. Water soluble surfactants are preferred, but organosoluble compounds can be used advantageously, especially if a solution of the surfactant can be introduced into the composition from which a spreading layer is formed or into the layer itself.

In use, the surfactant is appropriately included in the spreading layer in an amount effective to normalize spreading within the layer. This is usually from about 1 percent to about 15 percent. Unless expressly identified to the contrary, reference herein to percentage concentrations means percent by weight of total solids within the layer in which the designated item is located. Preferably, the surfactant is provided in the spreading layer in an amount of about 1 percent to about 10 percent and most preferably from about 3 percent to about 6 percent. In calculating the surfactant concentration, adjustment should be made for non-active ingredients in any surfactant composition. Expressed in terms of coverage, surfactant concentrations usually range from about 1.0 to about 6.0 grams per square meter.

The manner in which the surfactant normalizes spreading is not fully understood, but it is believed that an effective amount of surfactant may decrease the water of hydration of proteins within an aqueous liquid sample such that a greater amount of the sample's water and dissolved analyte are able to penetrate rapidly into both the spreading layer and the reagent layer. The rapid penetration speeds up the rate of indicating reactions and also encourages the formation within the element of equivalently sized sample wetted regions.

Reagent layers in the elements of this invention are permeable, and optionally porous if appropriate, to substance spreadable within the metering or spreading layer or to reaction products thereof. As used herein the term permeability includes permeability arising from porosity, ability to swell or any other characteristic. Reagent layers can include a matrix in which an interactive material in distributed, i.e., dissolved or dispersed. The choice of a matrix material is, of course, variable and dependent on the intended use of the element. Desirable matrix materials can include hydrophilic materials such a hydrophilic colloids, preferably in the form of a water-swellable gel. Useful hydrophilic materials include both naturally occuring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use for which a particular element is intended.

To enhance permeability of the reagent layer, if not porous, it is often useful to use a matrix material that is swellable in the solvent or dispersion medium of liquid under analysis. The choice of a reagent layer matrix, in any given instance, may also depend in part on its optical or other properties that could affect radiometric detection. The reagent layer should be noninterfering with respect to any intended result detection procedure. Also, it may be necessary to select material that is compatible with the application of an adjacent layer, such as by coating means, during preparation of the element. As an example, where the formation of discrete layers is desired and the intended analysis will be of aqueous liquids, it may be appropriate to select an essentially water soluble matrix for the reagent layer and essentially organosoluble or organodispersible ingredients for an adjacent layer, such as a spreading layer. In such manner, mutual solvent action is minimized and a clearly delineated layer structure can be formed. In many cases, to facilitate the formation within the spreading layer of such apparent concentrational uniformity as is discussed herein, it may be desirable to have the reagent layer of lower permeability than is the spreading layer itself. Relative permeability can be determined by well-known techniques.

In various preferred embodiments of the present elements, the interactive material in the reagent layer interacts with the analyte material to which the element is responsive. In other embodiments, the interactive material can interact with a precursor or a product of an analyte, as appropriate in view of the analysis mechanism of choice. The term "interactive" is meant herein to refer to chemical reactivity such as reactivity by addition, protonation, decomposition, etc., activity as in the formation of an enzyme-substrate complex, activity as is produced as a result of enzymatic action as well as any other form or composition of chemical or physical interaction able to produce or promote within the element, such as in the reagent layer, the formation of a radiometrically detectable change, i.e., one that is detectable by suitable measurement of light or other electromagnetic radiation.

The distribution of interactive material can be obtained by dissolving or dispersing it in the matrix material. Although uniform distributions are often preferred, they may not be necessary if the interactive material is, for example, an enzyme. Reagents or other interactive materials soluble in the liquid under analysis may advantageously be immobilized in the reagent layer, particularly when the reagent layer is porous.

The particular interactive materials that may be distributed within a reagent layer will depend on the analysis of choice. In the case of glucose anaylsis, a ferricyanide compound can be used. Glucose reacts with ferricyanide and the reaction causes a decrease in the yellow color characteristic of ferricyanide. In testing for uric acid, as in blood of serum, a mixture of copper sulfate and neocuproine can be distributed in the reagent layer matrix. Uric acid causes reduction of cupric copper to cuprous copper that can complex with the neocuproine to form a colored material that is proportional in density to the concentration of uric acid in the analyzed liquid. In the case of many analyses, enzymes such as oxidase materials like glucose oxidase may desirably be included as interactive materials within a reagent layer of an element intended for the anaylsis of analyte that is a substrate for such enzyme. As an example, an oxidative enzyme can be incorporated into a reagent layer together with peroxidase or a peroxidative material and a chromogen material or composition that, upon oxidation in the presence of peroxidase (or another substance having peroxidative activity) and the hydrogen peroxide formed upon interaction of an oxidase and its substrate, provides a dye or other detectable species. An interactive material that, upon appropriate interaction, provides directly a detectable change in the element is also termed an indicator. A plurality of materials, including at least one interactive material, that act together to provide a detectable change in the element is collectively termed an indicator composition.

Chromogenic materials or compositions that contain an oxidizable moiety and can provide a detectable species include certain dye-providing materials or compositions. In one aspect, a dye can be provided by a compound that, when oxidized, can couple with itself or with its reduced form to provide a dye. Such autocoupling compounds include a variety of hydroxylated compounds such as orthoaminophenols, alkoxynaphthols, 4-amino-5-pyrazolones, cresols, pyrogallol, guaiacol, orcinol, catechol phloroglucinol, p,p-dihydroxydiphenyl, gallic acid, pyrocatechoic acid, salicyclic acid, etc. Compounds of this type are well known and described in the literature, such as in *The Theory of the Photographic Process*, Mees and James Ed. (1966), especially at Chapter 17. In another aspect, the detectable species (dye) can be provided by oxidation of a leuco dye to provide the corresponding dye-stuff form. Representative leuco dyes include such compounds as leucomalachite green and leucophenolphthalein. Other leuco dyes, termed oxichromic compounds, are described in U.S. Pat. No. 3,880,658. The non-stabilized oxichromic compounds described in U.S. Pat. No. 3,880,658 are considered preferable in the practice of this invention. In yet another aspect, the detectable species can be provided by dye-providing compositions that include an oxidizable compound capable of undergoing oxidative condensation with couplers such as those containing phenolic groups or activated methylene groups, together with such a coupler. Representative such oxidizable compounds include such compounds as benzidene and its homologs, p-phenylenediamines, p-aminophenols, 4-aminoantipyrine, etc. A wide range of such couplers, including a number of autocoupling compounds, is described in the literature, such as in Mees and James (supra) and in Kosar *Light-Sensitive Systems*, 1965, pages 215-249.

Preferred dye-providing materials or compositions include 4-methoxy-1-naphthol, an autocoupling species, and the combination of 4-aminoantipyrine (HCl) as an oxidizable compound together with 1,7-dihydroxynaphthalene as a coupler.

In preparing integral analytical elements of this invention, the layers can be preformed separately and thereafter brought together to form the overall element. The layers can be laminated prior to use or maintained as separate layers until brought into fluid contact when the element is in use. Layers prepared in such a manner are typically coated from solution or dispersion on a surface from which the dried layer can be physically stripped. However, a convenient method which can avoid multiple stripping and lamination steps is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques wellknown in the preparation of light-sensitive photographic films and papers. If it is essential or desirable that adjacent layers be discrete, and maintenance of layer separation by adjustment of coating formulation specific gravity is not satisfactory, as possibly in the case of porous spreading layers, the appropriate selection of components for each layer, including solvent or dispersion medium, can minimize or eliminate interlayer component migration and solvent effects, thereby promoting the formation of well-defined, discrete layers. Any interlayer adhesion problems can be overcome without harmful effect by means of surface treatments including extremely thin application of subbing materials such as are used in photographic films.

For reagent layers, a coating solution or dispersion including the matrix and incorporated interactive materials can be prepared, coated as discussed herein and dried to form a dimensionally stable layer. The thickness of any reagent layer and its degree of permeability are widely variable and depend on actual usage. Dry thicknesses of from about 10 microns to about 100 microns have been convenient, although more widely varying thicknesses may be preferable in certain circumstances. For example, if comparatively large amounts of interactive materials, e.g., polymeric materials like enzymes, are required, it may be desirable to use slightly thicker reagents layers.

In addition to its permeability and radiation-transmissiveness as appropriate under circumstances of use, the reagent layer is desirably substantially free from any characteristic that might appear as or contribute to mottle or other noise in the detection of an analytical result produced in an integral element of the invention. For example, any variations in color or in texture within the reagent layer, as could occur if fibrous materials, e.g., some papers, are used as a permeable medium, may be disadvantageous due to non-uniform reflectance or transmittance of detecting energy. Further, although fibrous materials like filter and other papers are generally permeable overall, they typically can exhibit widely ranging degrees of permeability and may not exhibit suitable uniform permeability, for example, based on structural variations such as fiber dimensions and spacing. For such reasons, and further in view of reasons discussed hereinabove, such materials are not preferred in reagent or spreading layers of the present elements. Desirably, both spreading layers and reagent layers as discussed herein are formed from non-fibrous materials. It will be appreciated that it may be possible to use fibrous materials in appropriate combination with the non-fibrous materials.

Spreading layers can also be prepared by coating from solution or dispersion. As stated previously, spreading and associated layers of an element are in a superposed relationship such that a spreading layer is in fluid contact with a reagent layer, at least under conditions of use. The range of materials useful for preparing spreading layers is widely variable as discussed herein and, in addition to a surfactant as discussed previously, will usually include predominantly materials that are resistant to, i.e., substantially insoluble in and substantially non-swellable upon contact with, water or other solvent medium of liquid under analysis. Swelling of about 10–40% of the layers's dry thickness may be normal. The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements.

When preparing an isotropically porous spreading layer, it is useful to have void volume comprise at least about 25% of the total layer volume, and void volumes of from 50-95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when blush polymers are used in the isotropically porous spreading layer. The void volume of any such layer can be calculated with reasonable accuracy by a variety of techniques such as the statistical method described in Chalkley, *Journal of the National Cancer Institute*, 4, 47 (1943) and by direct weighing and determining the ratio of actual weight of the layer to the weight of solid material equal in volume to that of the layer, comparably composed of constituents from the layer. It will be appreciated that the pore size in any case should be sufficient to permit spreading of sample components desirably provided to a reagent layer.

As mentioned previously herein, the integral analytical elements can be self-supporting or coated on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials. For fluorimetric detection of analytical results through the support, it is desirable for the support to transmit over a somewhat wider band than is necessary for non-fluorescence measurements, or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, a reagent layer will usually be interposed in the element between the support and a spreading layer, which often is the outermost layer in an element.

The components of any particular layer of an integral analytical element of this invention, and the layer configuration of choice, will depend on the use for which an element is intended. As stated previously, spreading layer pore size can be chosen so that the layer can filter out undesirable sample components that would, for example, interfere with an analytical reaction or with the detection of any test result produced within the element. For analysis of whole blood, porous layers having a pore size of from 1 to about 5 microns are particularly useful in screening out blood cells, which typically have a size of from about 7 to about 30 microns. If desirable, an element can include a plurality of spreading layers, each of which may be different in its ability to spread and filter. Also, if a restraint on transport of substances within the element additional to that provided by spreading layers is needed, a filter or dialysis layer can be included at an appropriate location in the element. As an example, in analyzing for blood glucose, a dialysis layer such as a semipermeable cellulose membrane can prevent passage of proteins or other potentially interfering substances to the reagent layer.

It can also be desirable to include within an element one or more reflective layers, optionally absorptive to detecting radiation, such as to facilitate result detection by reflection radiometry, e.g., reflection photometry or a similar technique. Such reflectance can be provided by a layer also serving, for example, as a spreading layer or it can be provided by an additional layer that may not have an additional function within the element. Pigments, such as titanium dioxide, zinc oxide and barium sulfate and the like, are reflective and can be used to advantage in a reflecting layer. Blush polymers can also constitute a suitable reflecting material. As can be appreciated, pigment spreading layers may be useful for this purpose as can blushed polymer layers that may also be spreading layers. In one preferred aspect, blush polymer layers can also incorporate a pigment to enhance spreading and/or reflectivity. The amount of pigment that can be included in a layer together with blushed polymer is highly variable, and amounts of from about .2 to about 10 parts by weight of pigment per part by weight of blush polymer are preferred, with from about 2 to about 6 parts pigment per part of blush polymer being most preferred.

In layers of the element it can also be desirable to include materials that can render non-active in the analysis of choice, by chemical reaction or otherwise, materials potentially deleterious to such analysis. As an example, ascorbate oxidase may be incorporated in an element to remove ascorbate ion which may interfere with analysis for glucose.

To facilitate the detection of any change produced in an element as described herein, such as change in coloration, optical density or fluorescence, it can be desirable for the element to include a layer to receive any reaction products of other materials, the relative presence or absence of which characterizes the analytical result. Such a layer, conveniently referred to as a registration layer, is desirably in fluid contact with a reagent layer and may be separated from such reagent layer by a reflecting and/or opaque layer to facilitate the result detection by various radiometric techniques. Registration layers are desirably radiation-transmissive and can include hydrophilic colloids, such as those useful in reagent layers. Additionally, where dyestuffs are produced in the element, the registration layer may contain mordant materials for the dye, such as those useful in color photographic films and papers. Registration layers are discussed in greater detail in U.S. Pat. Application Ser. No. 598,462, filed July 23, 1975 in the name of Pierre L. Clement.

Analytical elements of the present invention can be adapted for use in carrying out a wide variety of chemical analyses, not only in the field of clinical chemistry but in chemical research and in chemical process control laboratories. They are well suited for use in clinical testing of body fluids, such as blood, blood serum and urine, since in this work a large number of repetitive tests are frequently conducted and test results are often needed a very short time after the sample is taken. In the field of blood analysis, for example, the multilayer element can be adapted for use in carrying out quantitative analyses for many of the blood components which are routinely measured. Thus, for example, the element may be readily adapted for use in the analysis of such blood components as urea nitrogen, chloride, glucose and uric acid, as well as many other components, by appropriate choice of test reagents or other interactive materials. In analyzing blood with an analytical element of this invention, the blood cells may first be separated from the serum, by such means as centrifuging, and the serum applied to the element. However, it is not necessary to make such separation, especially if reflective spectrophotometric analysis techniques are used to quantify or otherwise analyze the reaction product formed in the element as whole blood can be applied directly to the element and the blood cells filtered out through the action of a filtering layer. The presence of these cells on the element will not interfere with spectophotometric analysis if it is carried out by reflection techniques, with light being transmitted through the support and registration layer and reflected from the radiation-blocking layer or other reflecting layer such that the cells do not intercept detecting radiation. A particularly significant advantage of the integral analytical elements described herein is their ability to be used to analyze either serum or whole blood without need for any wipe-off or other sample removal step.

As can be appreciated, a variety of different elements, depending on the analysis of choice, can be prepared in accordance with the present invention. Elements can be configured in a variety of forms, including elongated tapes of any desired width, sheets or smaller chips. Particular elements can be adapted for one or more tests of a single type or a variety of tests of different types. In such latter event, it can be desirable to coat a common support with one or more strips or channels, each optionally of a different composition to form a composite element suited for conducting a variety of desired tests.

Figure 2:
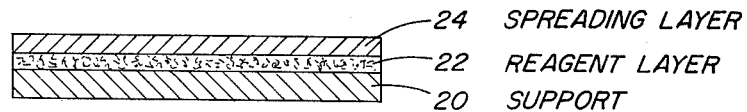
Figure 3:
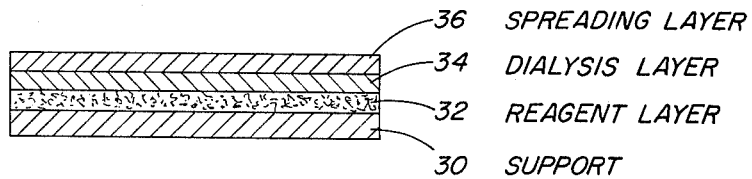
FIG. 3 is an enlarged sectional view of a preferred embodiment illustrating an integral analytical element of this invention. Each of FIG. 4, FIG. 5, FIG. 6

Exemplary elements of this invention include those illustrated in the accompanying drawings. In FIG. 1 is represented an analytical element composed of a radiation-transmissive support 10, on which is coated a reagent layer 12, a reflecting layer 14 which provides an appropriate background for analytical result detection, such as by reflection spectrophotometry, a filtering layer 16, and a sample spreading layer 18. Detection can be done through the support, if suitably transmissive at the detecting wavelength. Reagent layer 12 can be composed of a solution or dispersion of one or more test reagents in a binder such as gelatin, while each of layers 14, 16 and 18 can be a blush polymer having isotropic porosity and/or pore size as may be needed for the particular function each layer is intended to perform. The spreading layer 18 and the reagent layer 12 will be in fluid contact. In an alternative embodiment of the invention shown in FIG. 2, the analytical element is composed of a support 20 bearing a reagent layer 22 in fluid contact with a spreading layer 24 which can also serve the function of filtering and also may provide a suitably reflective background for reflection spectrophotometric detection through support 20. Alternatively, layer 24 may be such that it does not reflect and detection can be accomplished in the transmission mode. Layer 24 can be, for example, an isotropically porous blush polymer layer which has been coated or laminated over layer 22. FIG. 3 illustrates a further embodiment of the invention in which the analytical element is composed of a support 30, a reagent layer 32, a dialysis layer 34 which can be formed from a semipermeable membrane and a spreading layer 36, such as an isotropically porous blush polymer layer, which can serve the functions of spreading and filtering and which can provide a suitable background for reflection spectrophotometry through support 30. The spreading layer and reagent layer are in fluid contact.

The present elements are placed in use by applying to the element a sample of liquid under analysis. Typically, an element will be formed such that an applied sample will contact a spreading layer prior to a non-spreading reagent layer and will first contact the spreading layer at its surface farther from a reagent layer. Because analytical accuracy of the present elements is not substantially diminished by variations in the volume of applied samples, due to the novel relationship of spreading layer and fluid contacting reagent layer, sample application by hand or machine is acceptable. For reasons of convenience in detecting an analytical result, however, reasonable consistency in sample volume may be desirable. The spreading layer is also extremely desirable in minimizing the occurrence of ringing when soluble interactive materials are used in a reagent layer.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by the spreading layer, the element is exposed to any conditioning, such as heating, humidification or the like, that may be desirable to quicken or otherwise facilitate obtaining any test result. If an automated procedure is used, it can also be desirable to have the spreading layer accomplish its function within several seconds. This can be accomplished conveniently by appropriate selection of various spreading layer parameters, such as layer thickness, void volume in porous layers, etc.

After the analytical result is obtained as a detectable change, it is measured, usually by passing the element through a zone in which suitable apparatus for reflection, transmission or fluorescence spectrophotometry is provided. Such apparatus would serve to direct a beam of energy, such as light, through the support which is then reflected from the element back to a detecting means or passes through the element to a detector in the case of transmission detection. In a preferred mode, the analytical result is detected in a region of the element totally within the region in which such result is produced. Use of reflection spectrophotometry can be advantageous in some situations as it effectively avoids optical interference from any residues, such as blood cells, which have been left on or in the layers of the element. Conventional techniques of fluorescence spectrophotometry can also be employed if desired. Furthermore, when blood serum is tested or means are provided for eliminating unwanted whole blood residues, transmission techniques can be used to detect and quantify the indicating reaction products by directing a flow of radiant energy, for example, U.V. visible or I.R. radiation, at one surface of the element and measuring the output of that energy from the opposing surface of the element. Generally, electromagnetic radiation in the range of from about 200 to about 900 nm, or radiation due to radioactivity, have been found useful for such measurements, although any radiation to which the element is permeable and which is capable of quantifying the product produced in the reagent layer can be used. Various calibration techniques can be used to provide a control for the analysis. As one example, a sample of analyte standard solution can be applied adjacent to the area where the drop of sample is placed in order to permit the use of differential measurements in the analysis.

The following examples of analytical elements are provided to further illustrate the present invention.

EXAMPLE 1

To prepare a control integral analytical element, a transparent polyethylene terephthalate support was coated with a reagent layer including, after drying, ingredients as listed below and at the coverage indicated per square meter of support.

| | |
|---|---|
| Gelatin | 21.5 g/m² |
| 1-naphthosulfonic acid, sodium salt | 1.08 g/m² |
| 4-aminoantipyrine | 0.54 g/m² |
| glycerol | 2.15 g/m² |
| peroxidase | 7.000 Units/m² |
| glucose oxidase | 6.900 Units/m² |
| Surfactant 10G®* | 0.39 g/m² |

*Surfactant 10G is a p-isononylphenoxypolyglycidolether having 10 glycidol units, from Olin Mathieson Company Over the reagent layer was coated a spreading layer including, after drying, ingredients as listed below and at the coverages indicated per square meter of support.

| | |
|---|---|
| cellulose acetate (blush) | 6.6 g/m² |
| titanium dioxide | 46.0 g/m² |
| polyurethane elastomer (Estane® 5711; B. F. Goodrich Co.) | 1.38 g/m² |

Figure 4:
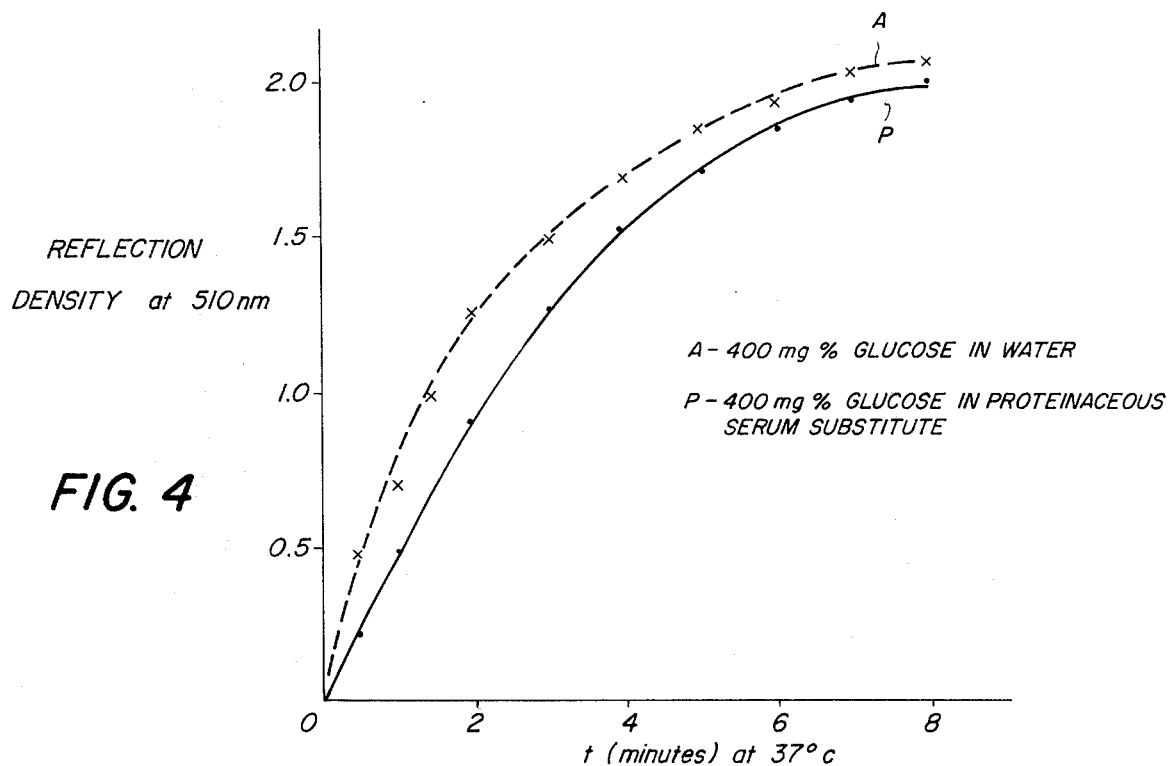

A first sample of the resultant element was spotted with 10 μl of a 400 mg% solution of glucose in water, and a second sample of the element was spotted with 10 μl of a 400 mg% solution of glucose in Versatol$^R$*. The reflection density of the colored dye spot produced in the reagent layer of the spotted elements was monitored for a period of 8 minutes, during which time the element samples were held at 37° C. Monitoring was accomplished by densitometer readings at 510 nm. The spreading layer provided a reflective background for the densitometric readings. After the eight minute incubation, the diameter of each colored spot was measured. At least two other sets of samples were similarly spotted and measured, both for reflection density and spot size. In each instance, the initial rate of dye generation, measured as $D_R$, was greater in element samples spotted with the non-proteinaceous glucose water. Further, the dye spot diameter of the glucose water spotted elements was approximately 20% larger than the dye spot size produced in element samples spotted with the Versatol$^R$ preparation. A graphical representation of the density produced over the 8 minutes for each of the two samples is provided in FIG. 4 of the drawings.

**Versatol is a reconstituted human serum substitute, standardized for 14 constituents at levels average for adults, and is supplied as a lyophilized powder by General Diagnostics, Division of Warner-Lambert Co. When the powder is dissolved per package instructions in deionized water, it gives 81 mg% glucose, 4.1 g% albumin and 3.0 g% total globulins (A/G ratio = 1.4).

The occurrence of 8 minute higher $D_R$ in the element spotted with glucose water is not understood in view of that sample having the larger dye spot. Usually, dye density varies inversely with the area of the dye spot. It is believed that in the absence of proteins such as are present in Versatol$^R$, some of the dye produced in the reagent layer diffused into the reflective, opaque spreading layer where it was not detected by the densitometric measurement of dye within the radiation-transmissive reagent layer.

EXAMPLE 2

Figure 5:
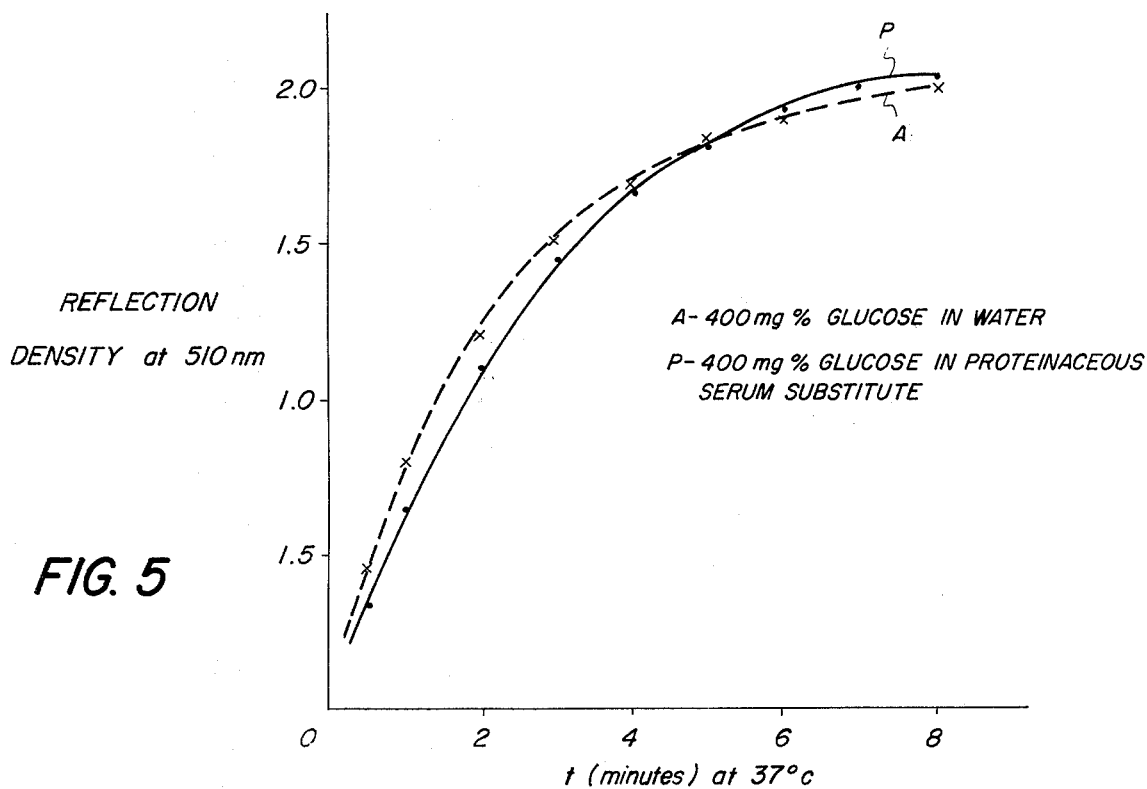

Elements were prepared as described in Example 1, except that the spreading layer also included 3.2 g/m² (5.9%) of a nonionic octylphenoxy polyethoxyethanol surfactant having approximately 9-10 ethoxy units. The surfactant was Triton $^R$ X-100 sold by the Rohm and Haas Company. Samples of this element were spotted and evaluated as described in Example 1. The density produced between elements spotted with glucose in water and glucose in Versatol$^R$ varied substantially less than did the density of comparable elements of Example 1, and the dye spot diameters between the spot produced by glucose and glucose in Versatol$^R$ varied by only about 8%. A graph representing the density produced in spotted elements made as described in Example 2 is provided in FIG. 5 of the drawings.

EXAMPLE 3

Figure 6:
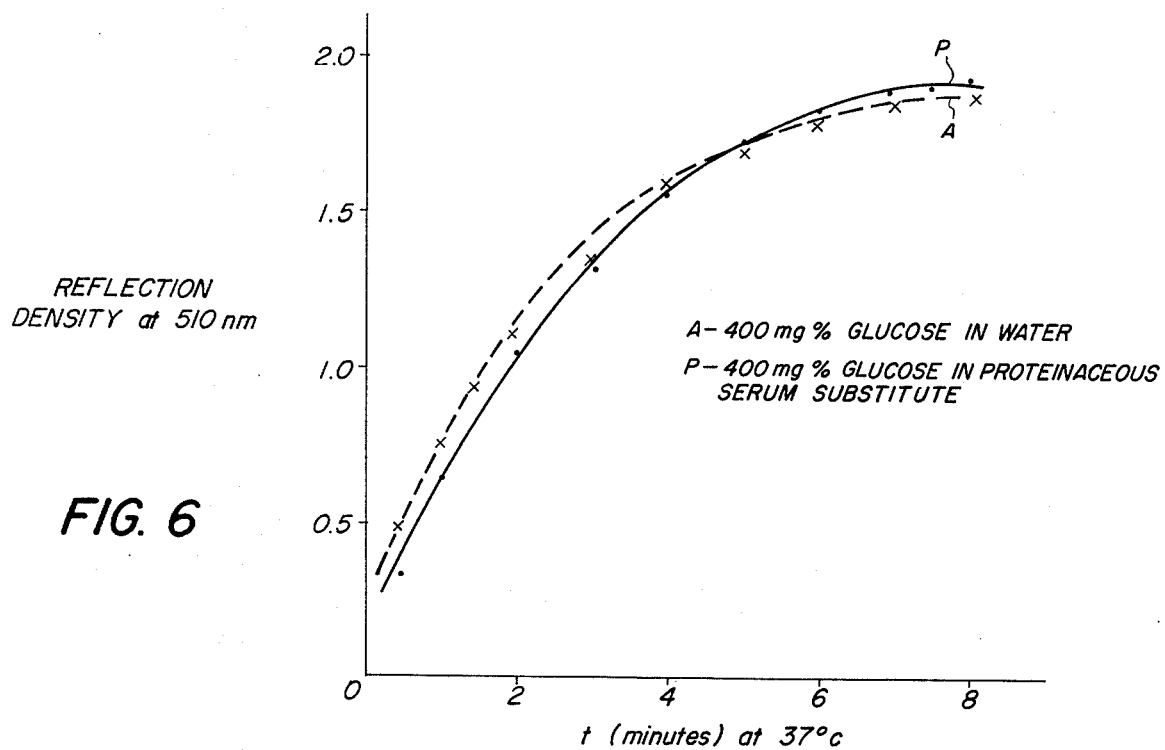

Analytical elements were prepared, spotted and evaluated as described in Example 2, except that the Triton$^R$ X-100 was included in the spreading layer at a coverage of 6.4 g/m² (11.8%). The density produced in the tested samples of this element was similar to the density produced on corresponding samples of the element described in Example 2 and a graph representing the density produced in spotted samples of an element made as described in this Example is provided in FIG. 6 of the drawings. The diameter between spots produced on samples of the present example by glucose in water and glucose in Versatol$^R$ varied by only about 9%.

EXAMPLE 4

Figure 7:
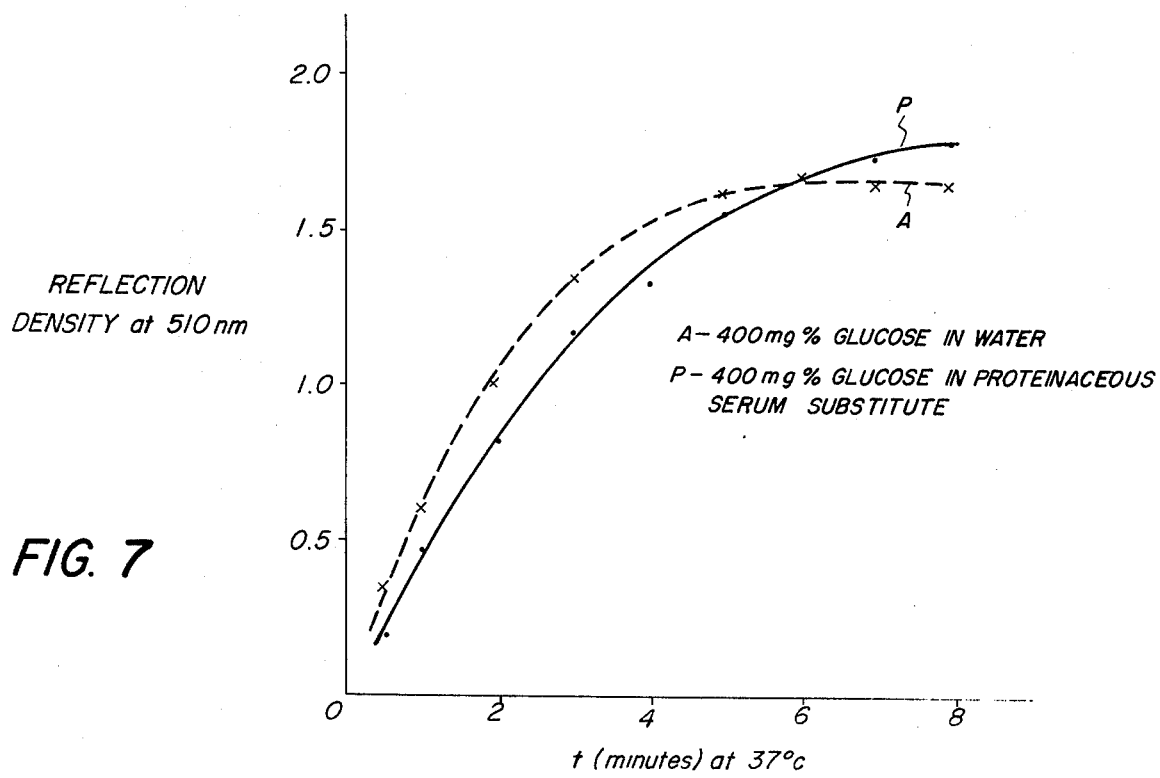
FIG. 7 is a graph illustrating an analytical result produced using an element described in the working Examples. The result illustrated in FIG. 4 is a control and the results illustrated in each of FIG. 5, FIG. 6

An analytical element was prepared, spotted and evaluated as described in Example 2, except that Triton$^R$ X-100 was included in the spreading layer at a coverage of 12.88 g/m² (23.6%). The density produced in tested samples of this element was less similar, comparing samples spotted with glucose in water and glucose in Versatol$^R$, than the density in comparable samples prepared as described in Examples 2 and 3. A graph representing the density produced in spotted samples of an element made as described in this Example is provided in FIG. 7 of the drawings. The dye spot diameters, comparing spots produced by glucose in water and glucose in Versatol$^R$, appeared to vary by about 12%, but some irregularity in the spot edges made this determination somewhat difficult.

Still higher concentrations of surfactant did not produce beneficial results and spot edges became increasingly irregular.

Beneficial results have also been obtained with similar experiments using equivalent amounts alkylphenoxypolyethoxyethanols with somewhat longer polyethoxy chains. A preferred compound is Triton$^R$ X-405, marketed by Rohm and Haas, an octylphenoxypolyethoxyethanol having approximately 40 ethoxy units.

The invention has been described in detail with particular reference to certain preferred embodiments thereof, but it will be understood that variations and modifications can be effected within the spirit and scope of the invention.

There is claimed:

1. An element for detection of analyte dissolved in proteinaceous, aqueous liquids, the element comprising an isotropically porous spreading layer and a reagent layer, wherein the spreading layer comprises a non-fibrous, water-resistant material and an non-ionic surfactant, the surfactant being present in an amount within the range of from about 1 to about 15 percent and effective to normalize liquid transport in the spreading layer.

2. An element as described in claim 1 wherein the surfactant is in the spreading layer in an amount of from about 1 percent to about 10 percent.

3. An element as described in claim 1 wherein the surfactant is in the spreading layer in an amount of from about 3 percent to about 6 percent.

4. An element for detection of analyte dissolved in proteinaceous, aqueous liquids, the element comprising an isotropically porous spreading layer and a reagent layer, wherein the spreading layer comprises a non-fibrous, water-resistant material and a non-ionic surfactant having the formula

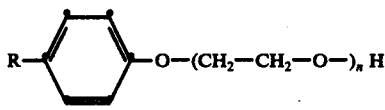

wherein R represents an alkyl group of from 1 to about 9 carbon atoms and $n$ represents an integer having a value of from about 5 to about 40, the surfactant being present in an amount within the range of from about 1 to about 15 percent and effective to normalize liquid transport in the spreading layer.

5. An element as described in claim 4 wherein the surfactant is present in an amount of from about 1 percent to about 10 percent.

6. An element as described in claim 5 wherein the surfactant is in the spreading layer in an amount of from about 3 percent to about 6 percent.

7. An element as described in claim 5 wherein the surfactant is an octylphenoxypolyethoxyethanol having from about 9 to about 40 ethoxy units.

8. An element as described in claim 7 wherein the surfactant is present in an amount of from about 1 percent to about 10 percent.

9. An element as described in claim 7 wherein the surfactant is in the spreading layer in an amount of from about 3 percent to about 6 percent.

10. An element for detection of analyte dissolved in proteinaceous, aqueous liquids, the element comprising an isotropically porous spreading layer and a reagent layer, wherein the spreading layer comprises a non-fibrous, water-resistant material and a non-ionic surfactant having the formula

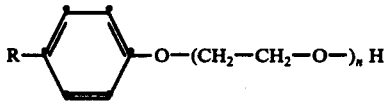

wherein R represents an octyl group or a nonyl group and $n$ represents 9, 10 or 40, said surfactant being present in an amount within the range of from about 1 to about 15 percent and effective to normalize liquid transport in the spreading layer.

11. An element as described in claim 10 wherein the surfactant is in said layer in an amount of from about 1 percent to about 10 percent.

12. An element as described in claim 11 wherein the surfactant is in the spreading layer in an amount of from about 3 percent to about 6 percent.

13. An element for detection of analyte dissolved in a proteinaceous, aqueous liquid, the element comprising a radiation transmissive support having thereon an isotropically porous spreading layer and a water-swellable reagent layer, wherein the reagent layer is interposed between the support and the spreading layer and wherein the spreading layer comprises a non-fibrous, water-resistant material and a non-ionic surfactant, the surfactant being present in an amount within the range of from about 1 percent to about 15 percent and effective to normalize liquid transport in the spreading layer.

14. An element as described in claim 13 wherein the surfactant is in the spreading layer in an amount of from about 1 percent to about 10 percent.

15. An element as described in claim 14 wherein the surfactant is in the spreading layer in an amount of from about 3 percent to about 6 percent.

16. An element for detection of analyte dissolved in a proteinaceous, aqueous liquid, the element comprising a radiation-transmissive support having thereon, in fluid contact, an isotropically porous spreading layer and a water-swellable reagent layer of lower permeability than the spreading layer, wherein the reagent layer is interposed between the support and the spreading layer and wherein the spreading layer comprises a non-fibrous, water-resistant material and a non-ionic surfactant having the formula

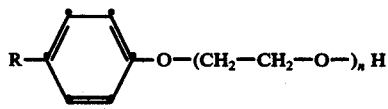

wherein R represents an alkyl group of from 1 to about 9 carbon atoms and $n$ represents an integer having a value of from about 5 to about 40, the surfactant being present in an amount effective to normalize liquid transport in the spreading layer.

17. An element for detection of analyte dissolved in a proteinaceous, aqueous liquid, the element comprising a radiation-transmissive support having thereon (a) an isotropically porous, water-resistant spreading layer comprising (i) a member selected from the group consisting of a non-fibrous, isotropically porous material and particulate matter, and (ii) a non-ionic surfactant having the formula

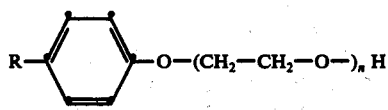

wherein R represents an alkyl group of from 1 to about 9 carbon atoms and $n$ represents an integer having a value of from about 5 to about 40, the surfactant being present in an amount within the range of from about 1 to about 15 percent and effective to normalize liquid transport in the spreading layer, and (b) a water-swellable reagent layer comprising a hydrophilic colloid matrix having distributed therein a material interactive in the presence of analyte or a precursor or a reaction product thereof to produce a detectable change in the element, wherein the reagent layer is interposed between the support and the spreading layer.

18. An analytical element as described in claim 17 wherein the surfactant is present in an amount of from about 1 percent to about 10 percent.

19. An element for detection of analyte dissolved in a proteinaceous, aqueous liquid, the element comprising a radiation-transmissive support having thereon (a) an isotropically porous, water-resistant spreading layer comprising (i) a member selected from the group consisting of a blush polymer, a colloid derived from a polymer, and a pigment, and (ii) a surfactant having the formula

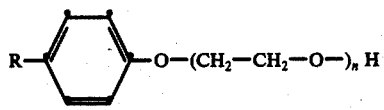

wherein R represents an alkyl group of from 1 to about 9 carbon atoms and $n$ represents an integer having a value of from about 5 to about 40, the surfactant being present in an amount within the range of from about 1 to about 15 percent and effective to normalize liquid transport in the spreading layer, and (b) a water-swellable reagent layer comprising a hydrophilic colloid matrix having distributed therein a material interactive in the presence of analyte or a precursor or a reaction product thereof to produce a detectable change in the element, wherein the reagent layer is interposed between the support and the spreading layer.

20. An analytical element as described in claim 19 wherein the surfactant is present in an amount of from about 1 percent to about 10 percent.

21. An element as described in claim 19 wherein the surfactant is an octylphenoxypolyethoxyethanol having from about 9 to about 40 ethoxy units.

22. An element as described in claim 21 wherein the surfactant is in the spreading layer in an amount of from about 3 percent to about 6 percent.

23. A method for determining the concentration of analyte dissolved in a proteinaceous, aqueous liquid, the method comprising (a) applying a sample of proteinaceous, aqueous liquid to an element comprising an isotropically porous spreading layer and a reagent layer, wherein the spreading layer comprises a non-fibrous, water-resistant material and a non-ionic surfactant in an amount within the range of from about 1 to about 15 percent and effective to normalize liquid transport in the spreading layer, to effect a detectable change in the element in the presence of an analyte within the sample, and (b) detecting any such change produced in the element.

* * * * *